US 6,709,109 B1

(12) United States Patent
Richards et al.

(10) Patent No.: US 6,709,109 B1
(45) Date of Patent: Mar. 23, 2004

(54) DIFFERENTIAL SPECTROSCOPIC IMAGING OF THE HUMAN RETINA

(75) Inventors: David W. Richards, Tampa, FL (US); Dennis K. Killinger, Tampa, FL (US); Anali Makoui, Temple Terrace, FL (US); Wyatt Saxon, Seffner, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/249,525

(22) Filed: Apr. 16, 2003

Related U.S. Application Data
(60) Provisional application No. 60/319,190, filed on Apr. 16, 2002.

(51) Int. Cl.[7] .................................................. A61B 3/10
(52) U.S. Cl. ........................................................... 351/221
(58) Field of Search .................................. 351/205, 206, 351/221, 245, 246, 213; 396/18; 600/473, 476, 558

(56) References Cited

U.S. PATENT DOCUMENTS 6,112,114 A * 8/2000 Dreher ........................ 600/476
6,179,421 B1 * 1/2001 Pang ............................ 351/205

FOREIGN PATENT DOCUMENTS

| WO | WO 97/30627 | 8/1997 |
| WO | WO 00/06015 | 2/2000 |
| WO | WO 01/78589 | 10/2001 |

OTHER PUBLICATIONS

Makoui, Anali, Optical Spectroscopy of Reflected Light from the Human Retina for Potential Diagnosis of Retinal Disease, Jun. 28, 2002.

* cited by examiner

*Primary Examiner*—George Manuel
(74) *Attorney, Agent, or Firm*—Anton J. Hopen; Smith & Hopen, P.A.

(57) ABSTRACT

The present invention includes a method of detecting nerve cell damage representative of glaucoma including the steps of: imaging a human retina in vivo, measuring the reflected light intensity at a first predetermined wavelength wherein values returned from healthy and damaged areas of retina are substantially identical, measuring a second reflected light intensity at a predetermined wavelength wherein values of healthy and damaged retina substantially diverge, and recording the differences between the first and second values, which values are indicative of glaucoma damage.

17 Claims, 12 Drawing Sheets

Damaged

Normal

DIFFERENTIAL SPECTROSCOPIC IMAGING OF THE HUMAN RETINA

CROSS REFERENCE TO RELATED APPLICATION

This disclosure claims the benefit of pending provisional patent application Ser. No. 60/319,190, filed on Apr. 16, 2002.

BACKGROUND OF INVENTION

1. Field of Invention

This invention relates to the detection and monitoring of retinal physiology and pathology, and more particularly to detecting damage to the retina caused by glaucoma.

2. Background of the Invention

Glaucoma is clinically characterized by recognizable patterns of visual field loss and optic nerve head pallor and excavation. Pathologically, there is atrophy of the ganglion cell and nerve-fiber layers of the retina. Glaucoma is the leading cause of irreversible blindness worldwide and the second leading cause in the United States, after macular degeneration.

The most widely accepted and heretofore effective means of diagnosing and monitoring glaucoma is the automated threshold-type visual field test such as performed by the Zeiss-Humphrey Model 750 Field Analyzer (Zeiss-Humphrey, Inc., Dublin, Calif.). Visual field tests are designed to map a person's visual field and document the level of peripheral vision. The test consists basically of responding every time a flash of light is perceived, all the while looking straight ahead. The test is computer controlled and lasts about five minutes per eye. Unfortunately, patients vary in their attentiveness and response time. Longer field tests are more likely to result in fatigue and diminish the ability of the patient to maintain peak concentration. Furthermore, there are many reasons other than glaucoma for an abnormal visual field result: (1) the test was poorly given due to technician error, (2) the instrument was defective, (3) the patient did not grasp how to take the test, (4) the patient was tired, (5) the defect is accounted for by some pathology other than glaucoma, such as a neurological disorder or retinal disease.

Accordingly, what is needed in the art is a fully objective and reliable technology for the detection and monitoring of the characteristic retinal damage caused by glaucoma.

It is, therefore, to the effective resolution of the aforementioned problems and shortcomings of the prior art that the present invention is directed.

However, in view of the prior art at the time the present invention was made, it was not obvious to those of ordinary skill in the pertinent art how the identified needs could be fulfilled.

SUMMARY OF INVENTION

The present invention includes a method of detecting nerve fiber layer and ganglion cell damage of the retina, representative of glaucoma, in vivo. It includes the steps of: imaging a retina, establishing a wavelength of light wherein reflections returned from healthy and damaged retina are substantially identical or similar. Baseline values for this wavelength have been empirically established at 500 nm or the spectral region from about 450 nm to about 600 nm. A second wavelength is determined wherein reflections from healthy and damaged retina substantially diverge. Such wavelengths have been empirically observed at 825 nm or the spectral region from about 750 nm to about 875 nm, although additional or specific wavelengths may be suitable. The differences between reflections at the first and second wavelengths are then recorded as a function of location on the retina and are used to provide a map of glaucoma damage. Measuring a plurality of wavelengths known to correlate with healthy and damaged pathology would lead to greater accuracy in an analysis. Such a map can be generated using analog or digital methods. A digital approach will most likely be easier to standardize and made available for widespread commercial use.

In a first embodiment of the invention, developed primarily for research purposes, a photographic slide of a human retina in vivo is obtained. A thermal (e.g., tungsten) light source is preferred for exposure of the photographic slide as flash sources may produce spectral lines. High-speed film (ISO 400) and a relatively low-light source, with an exposure of about one second is employed to obtain the necessary imaging and detail of a human retina in vivo. The slide is then illuminated by transmitted light by a tungsten, zirconium arc, or other thermal source lamp and focused onto a spectrometer. The retina is divided into a two-dimensional grid and each grid point is then plotted for the above-mentioned values. Wavelengths between 500 nm and 600 nm and between 750 nm and 875 nm have been empirically shown to differentiate healthy and damaged retinal layers. The relative difference between the spectral intensity of the first and second wavelengths may then be plotted in three-dimensional relation to the two-dimensional grid. Peaks or valleys on the grid are then indicative of retinal nerve-fiber layer and ganglion-cell layer damage, while a smooth uniform surface on the grid indicates a lack of pathology.

A second embodiment of the invention employs an array of band pass, low pass, or high pass filters to accept only the two wavelength bands of interest from the image of the retina (the baseline value and the variable value). As an in-vivo application, the image of the retina is split in two by an optical beam splitter and filtered. Synchronized CCD or video cameras capture the two images. The filtered images are then detected by the cameras and differenced using a computing means. An advantage of using the filters is that spectroscopic analysis is not needed and only the resulting intensities left after filtration need be examined.

A third embodiment of the invention employs single-wavelength or narrow line width lasers such as diode lasers or dye lasers or Optical-Parametric-Oscillator lasers which can tune to the spectral regions of interest. A laser is provided at the baseline wavelength (e.g. 500 nm) and at a wavelength sensitive to pathology. The reflection intensities of the retina at the wavelength of interest are mapped and analyzed to detect pathology.

An advantage of the present invention is that it provides a diagnostic tool for detecting and monitoring early and advanced visual field loss in glaucoma, and also for investigation of other retinal diseases such as macular degeneration and diabetic retinopathy.

Another advantage of the present invention is its ability to provide a diagnostic tool to examine a patient for suspected glaucoma even if there is no visual field loss.

Another advantage of the present invention is its ability to provide a rapid and objective diagnostic alternative to the traditional visual field test.

Another advantage of the present invention is its ability to provide a diagnostic tool that can differentiate between glaucoma and other disorders that might affect the traditional visual field test.

Another advantage of the present invention is its ability to provide a diagnostic tool that enables the study of low tension glaucoma.

Another advantage of the present invention is its ability to provide a diagnostic tool that produces consistent and reproducible results for long-term monitoring of a patient's retinal condition.

It is to be understood that both the foregoing general description and the following detailed description are explanatory and are not restrictive of the invention as claimed. The accompanying drawings, which are incorporated in and constitute part of the specification, illustrate embodiments of the present invention and together with the general description, serve to explain principles of the present invention.

These and other important advantages and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which.

DETAILED DESCRIPTION

Figure 1:
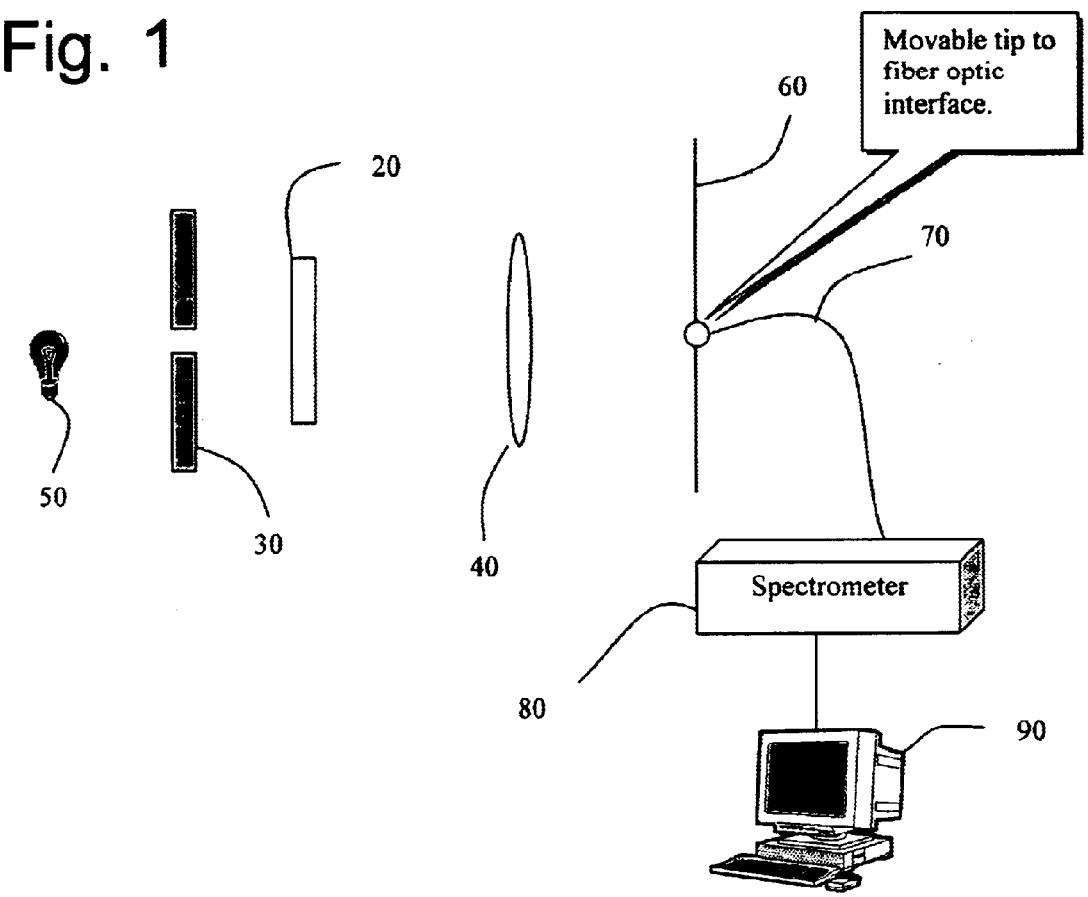
FIG. 1 is a diagrammatic view of a first embodiment of invention.

FIG. 1 shows a first embodiment of the invention. Traditional film photography has been used to produce a color transparency 20 of a patient's retina. Flash photography is not recommended to obtain the transparency because the flash may contain spectral lines. A spectral line is a component consisting of a very narrow band of frequencies isolated in a spectrum. Accordingly, a spectrally smooth output light source such as a thermal black-body-radiator light source or tungsten lamp is preferred. To mitigate the light intensity needed, and the potential for patient discomfort, high speed photographic film may be used. The patient should be still and a one second duration exposure is typically sufficient.

The slide transparency 20 is then disposed between a baffle and light aperture 30 and a double convex lens 40. A light source 50 is provided on the side of the baffle 30 opposite the slide transparency 20. The light source 50 illuminates the slide transparency 20 which image is then converged by the double convex lens 40 (preferably f=175 mm, D=50 mm) onto an image plane 60 having an optical fiber 70 (preferably 400 µm) optically connected to a spectrometer 80. The tip of the optical fiber may be adjusted to various positions behind the image plane 60 by mechanical means. For light source 50 a zirconium lamp was used which contains a zirconium oxide cathode in an argon-filled bulb, but there are other effective sources which may be employed as known to those skilled in the art.

Figure 2:
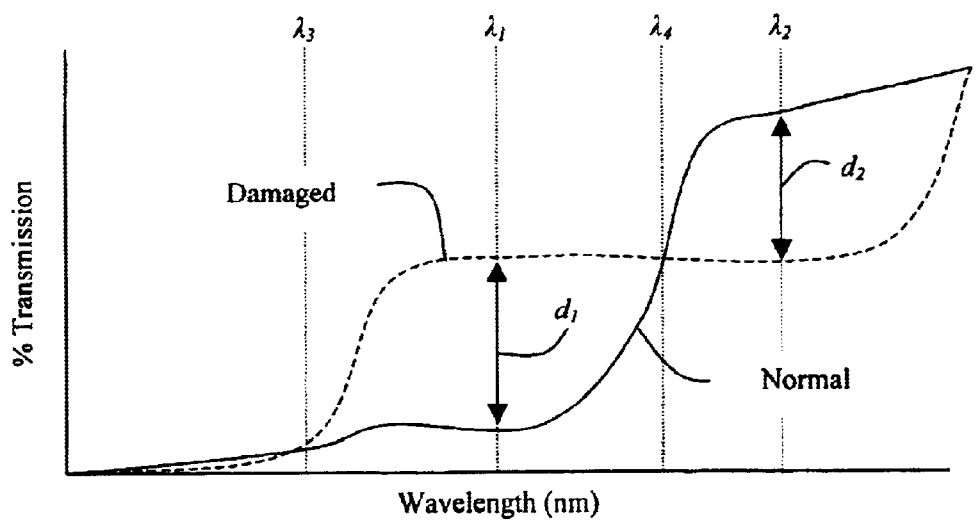
FIG. 2 is a graphic illustrating spectrometer readings as observed by the invention.

The spectrometer 80 is communicatively coupled to a computing means 90 for analyzing the reflection intensity of various locations on the patient's retina as represented by the transparency. In FIG. 2, the transmission spectrum of a damaged area of the retina is noted by line dashes and a normal area of the retina is noted by a solid line. At wavelength $\lambda_1$ the difference between the transmitted light intensity of the damaged and normal areas is noted as $d_1$. At wavelength $\lambda_2$ the difference between the transmitted intensities of the damaged and normal areas is noted as $d_2$. At wavelength $\lambda_3$ or $\lambda_4$ the difference between damaged and normal areas is nominal or nonexistent. Wavelength $\lambda_3$ or $\lambda_4$ is used for a baseline measurement to establish the relative intensity of the illumination of the retina so that transmission values for $\lambda_1$ and $\lambda_2$ are normalized. According to the first embodiment of the invention, the slide negative 20 is divided into a grid and measurements are analyzed at a plurality of plot points for at least one pair of wavelengths $\lambda_1$ and $\lambda_2$.

It should be noted that at baseline wavelengths, such as at 500 ($\lambda_3$) and 550 ($\lambda_4$) nm, the spectrum is essentially the same for normal and damaged retinal pathology. However, differences have been noted at 750–800 nm ($\lambda_1$) and 825–875 nm ($\lambda_2$). Accordingly, transmission values may be recorded at one or many wavelengths provided a difference is measurable.

Figure 3:
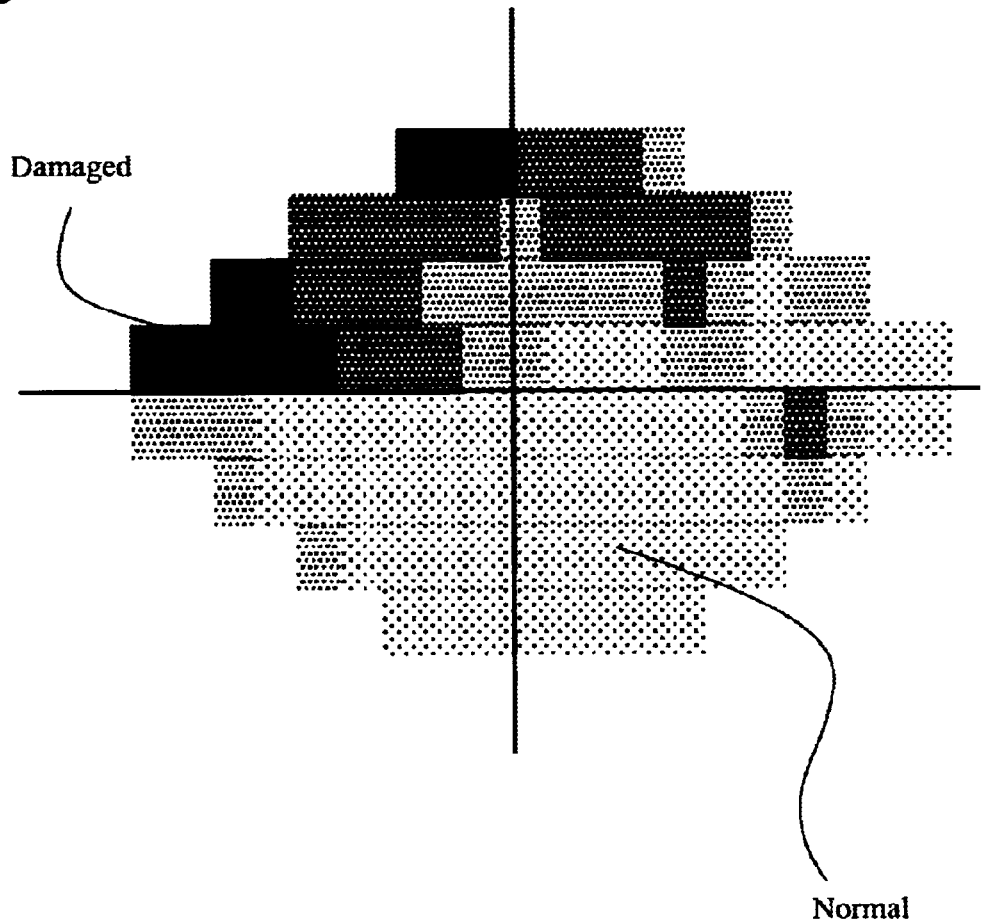
FIG. 3 is an illustrative graphic representation of a display output provided by the invention.

FIG. 3 illustrates a hypothetical output generated by the computing means 90 of FIG. 1. Darker areas are indicative of differences between transmission values at $\lambda_1$ and $\lambda_2$ for damaged retinal areas. Lighter areas are indicative of small or nonexistent differences thereof. The resultant output shown in FIG. 3 is purposefully similar to the traditional display obtained in automated visual field tests. However, far more detailed displays are possible due to the precise nature of the empirical spectra data obtained. For example, three dimensional or colorized topography displays may be generated. Furthermore, long-term monitoring of a patient's condition may be efficiently performed due to the speed and objective nature of the present invention.

Figure 4:
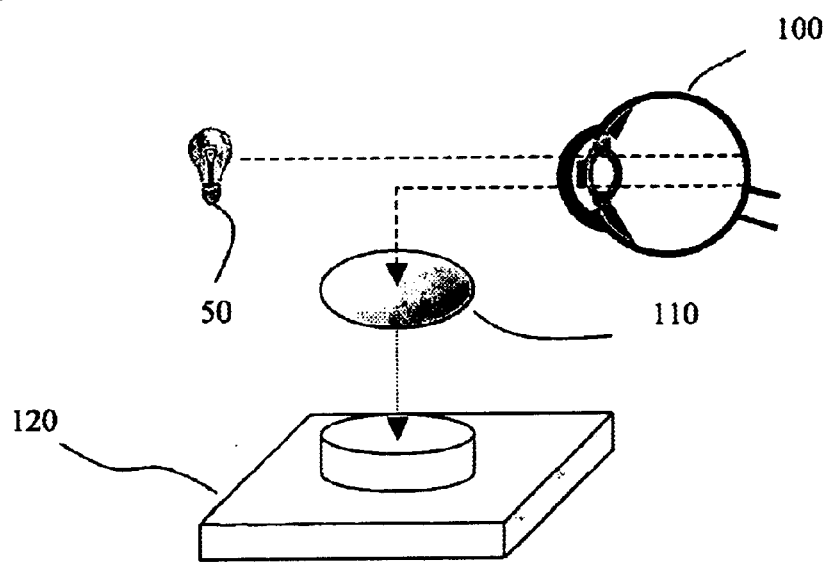
FIG. 4 is a diagrammatic view of an alternative embodiment of the invention employing narrow band optical filters.

Another alternative embodiment of the invention (FIG. 4) employs the light source 50 to illuminate a retina 100. A band pass filter 110 transmits only a limited part of the spectrum at the wavelength of interest. An image recording means 120 captures the resultant, filtered image. The image recording means 120 may include traditional film, a CCD, a video camera or the like.

Figure 5:
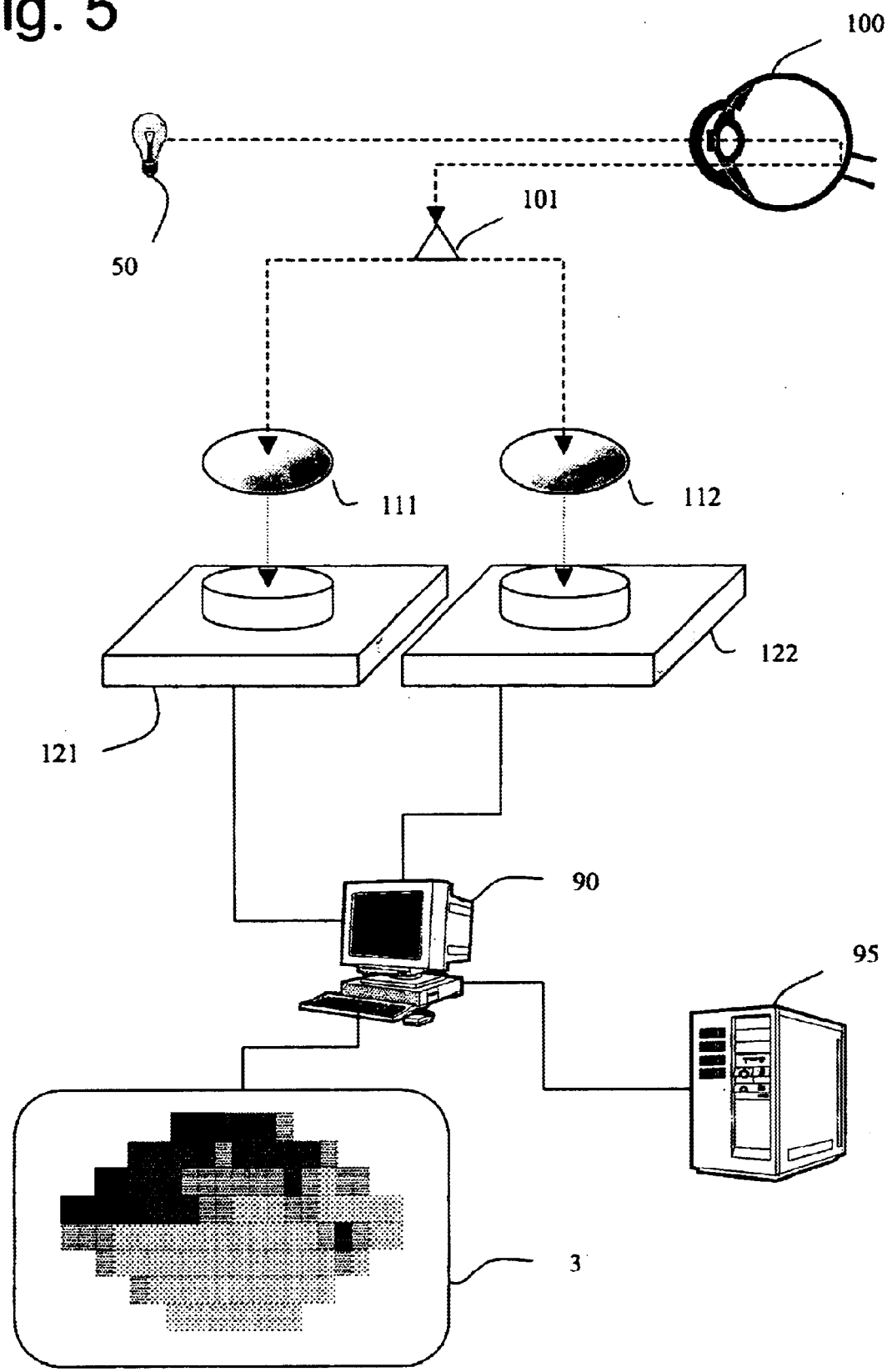
FIG. 5 is a diagrammatic view of an alternative embodiment of the invention wherein the image of the retina is simultaneously applied to a plurality of narrow band optical filters.

In FIG. 5, the light source 50 illuminates the retina 100. A beam splitter 101 sends the retinal image to a first filter 111 and a second filter 112. The first filter 111 permits one or more wavelengths between 550 and 750 nm to pass through and register on the first image recording means 121. The second filter 112 permits one or more wavelengths between 750 and 875 nm to pass through and register on the second image recording means 122. The proposed wavelengths are known to distinguish between healthy and damaged retinal pathology to the inventors.

However, additional wavelength ranges may be employed by those of ordinary skill in the art using the present disclosure.

The first and second image recording means 121–122 are communicatively coupled to the computing means 90 to render an output display 3 of the retinal pathology. A database store 95 may be used to aggregate records to monitor patient on a short-term or long-term basis.

Figure 6:
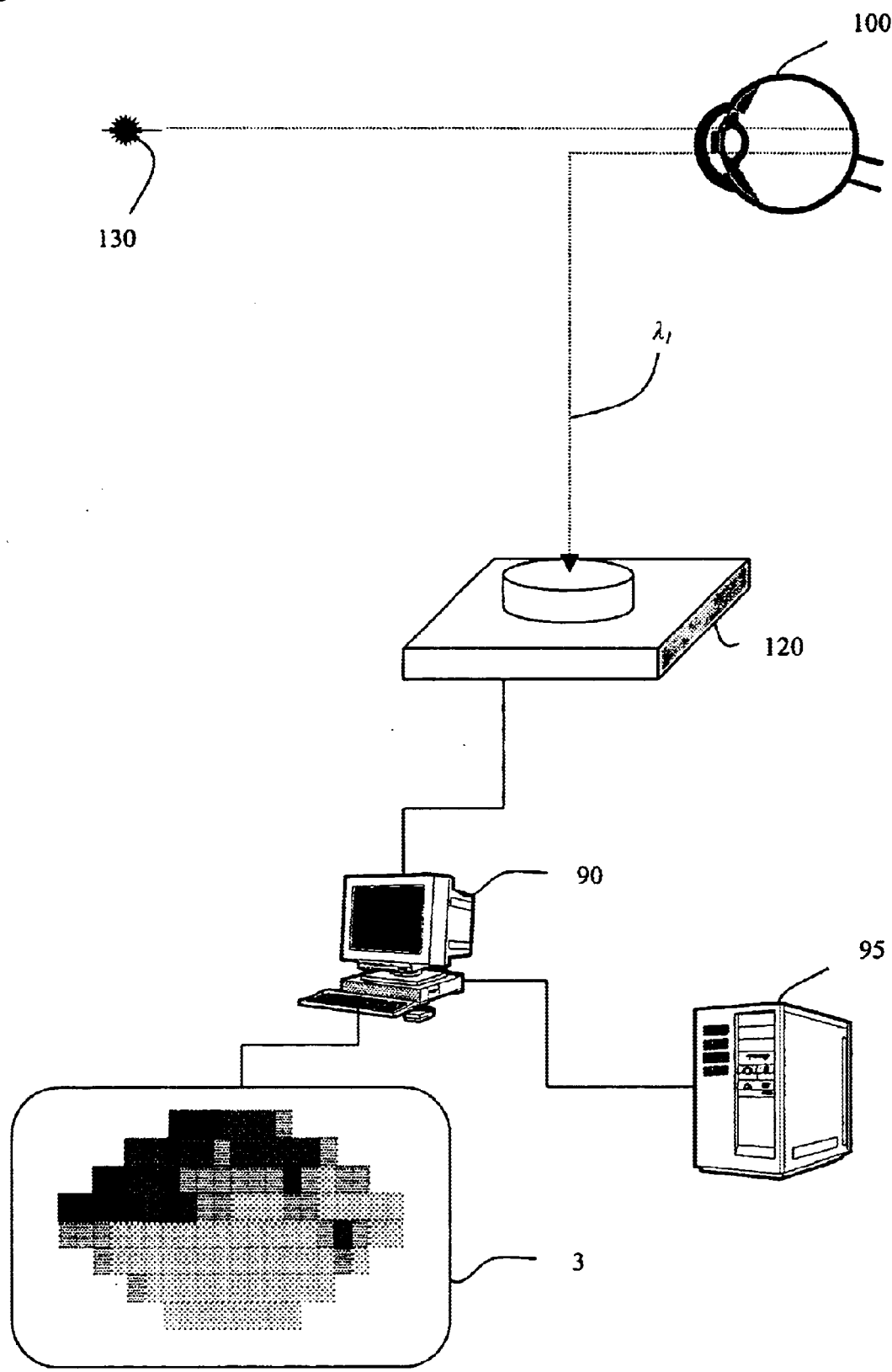
FIG. 6 is a diagrammatic view of an alternative embodiment of the invention wherein a single-wavelength laser illuminates the retina for analysis.

FIG. 6 illustrates yet another embodiment of the present invention comprising a single-wavelength laser 130 such as a He—Ne or diode laser. The laser 130 illuminates the retina 100 at a predetermined wavelength which is then registered by the image recording means 120. The advantage of using a single-wavelength laser is that narrow-band filters and spectrometers are not required. The single wavelength is chosen to correspond to that where reflectivity of normal and damaged retina differs the most.

Figure 7:
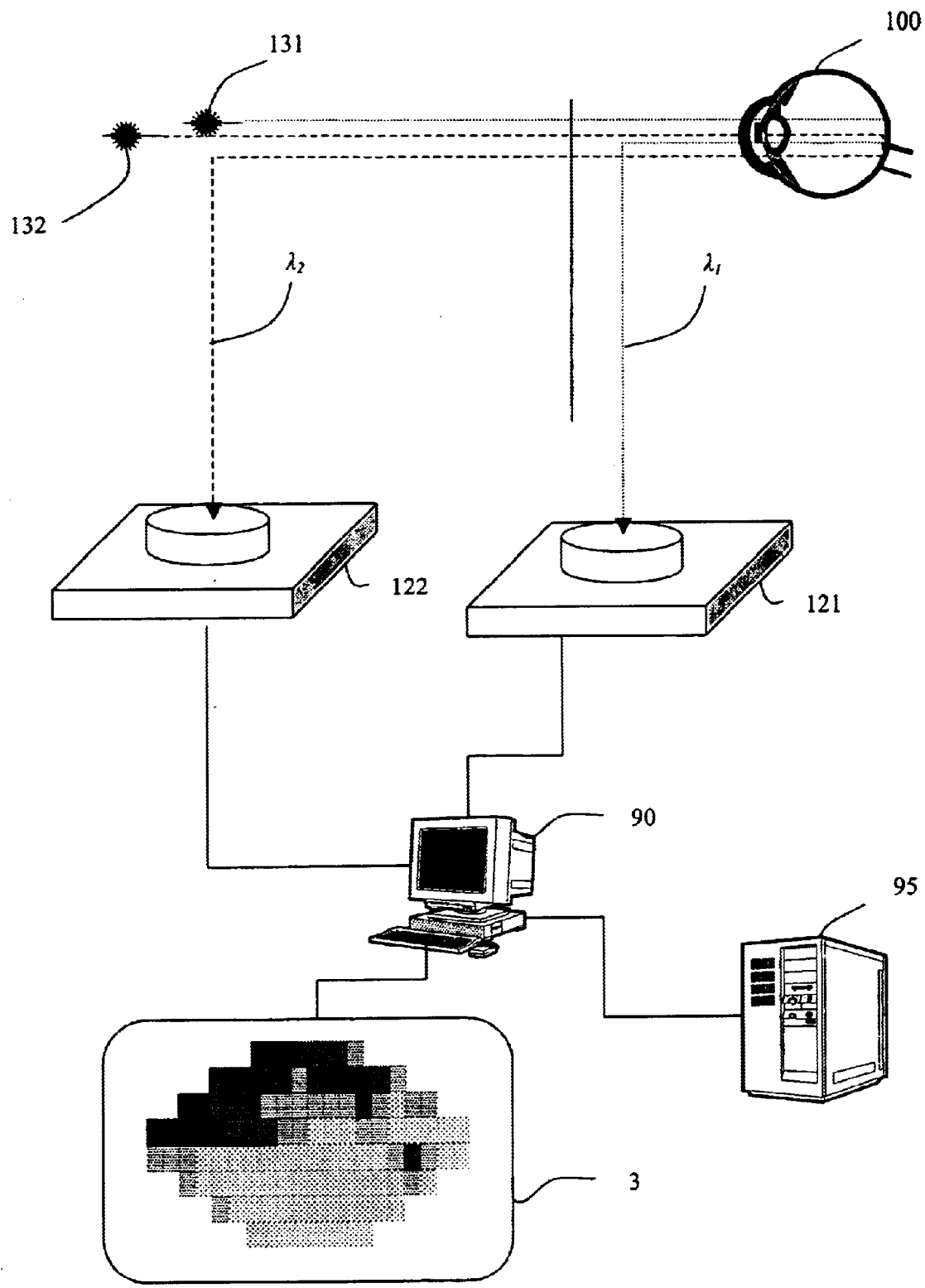
FIG. 7 is a diagrammatic view of an alternative embodiment of the invention wherein a plurality of single-wavelength lasers illuminates the retina for analysis.

FIG. 7 discloses an alternative embodiment to that shown in FIG. 6. A first laser 131 emits light into the retina 100 at wavelength $\lambda_1$ which is received by the first image recording means 121. A second laser 132 emits light into the retina 100 at wavelength $\lambda_2$ which is received by the second image recording means 122. By using a plurality of lasers, the resolution of the retinal pathology may be increased by sampling the retina at more than one wavelength. One or more wavelengths are selected to correspond to retinal pathology. One or more other wavelengths are selected as references for comparison.

Figure 8:
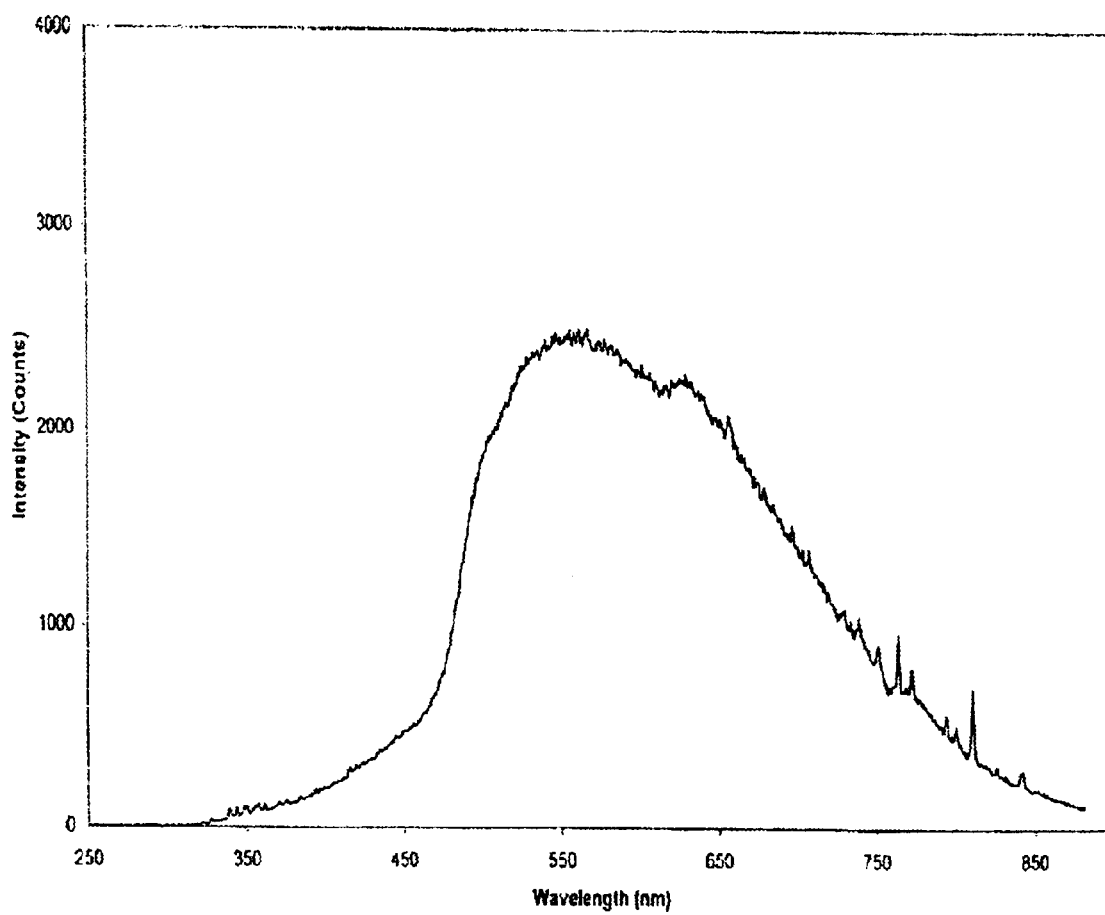
FIG. 8 is the spectrum intensity of the zirconium lamp used as reference and white light source for illuminating the slide.
Figure 9:
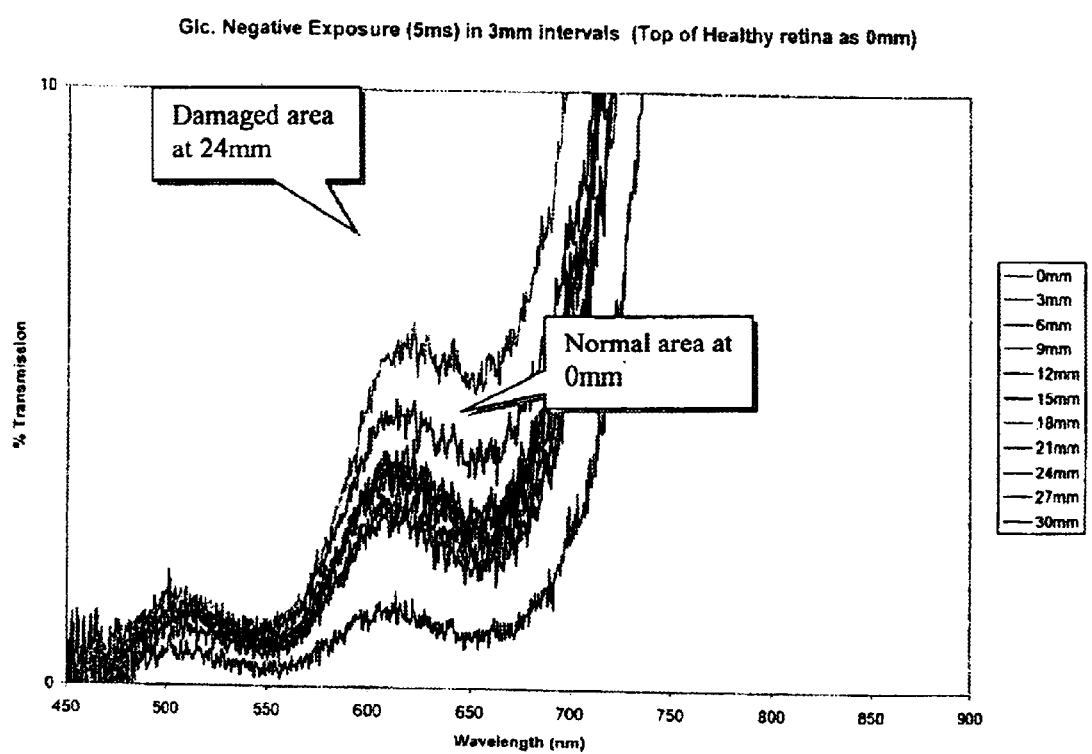
FIG. 9 is the transmission spectrum of a retina known to have glaucoma damage between 15–30 mm from the top of the eye, but to have normal pathology from 0–15 mm.
Figure 13:
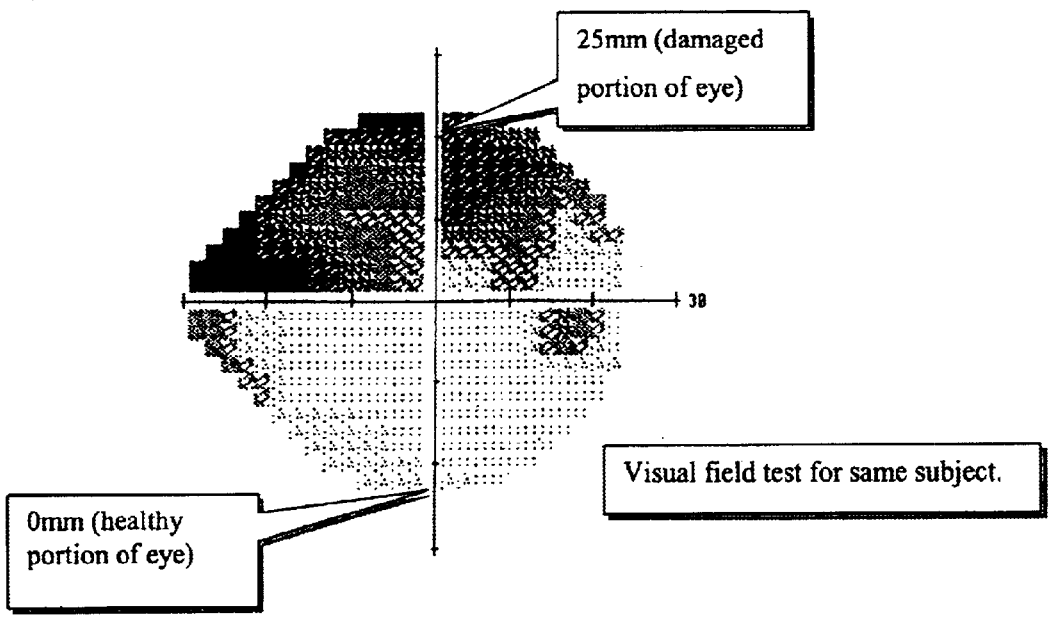
FIG. 13 is a visual field test for the same subject.
Figure 14:
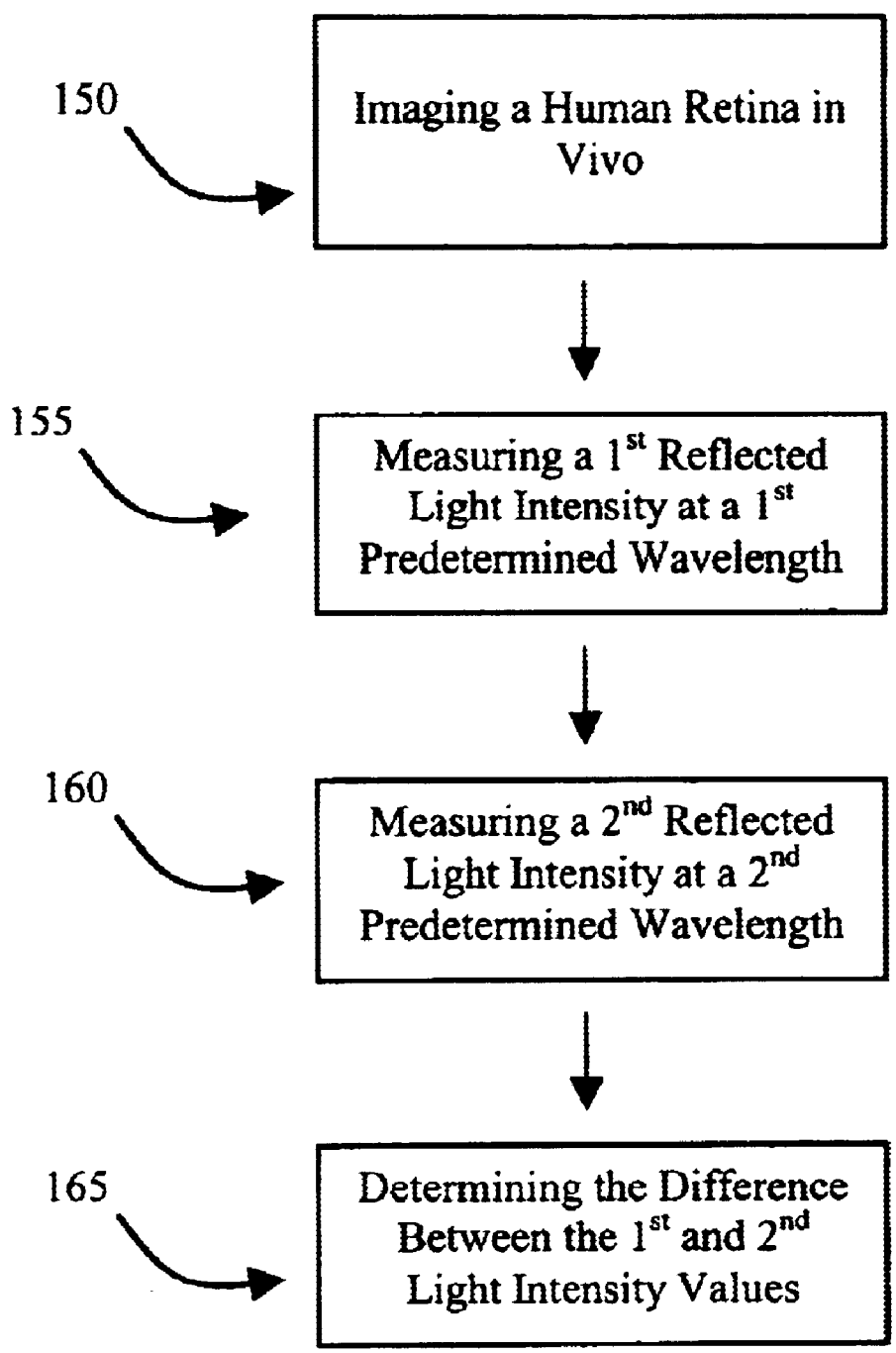
FIG. 14 is a flow diagram of the method of the present invention.

FIG. 8 is the spectrum intensity of the zirconium lamp used as reference and white light source for illuminating the slide in FIG. 1. FIG. 9 is the transmission spectrum of the slide image of a retina known to have glaucoma damage affecting the inferior hemi-retina; but with no damage to the superior hemi-retina. The actual visual field test for the same subject is shown in FIG. 13. Note that the visual field, which is mapped as the patient sees the world, is inverted with respect to the region of retinal damage. In FIG. 13, it can be deduced that the lower portion of the retina (corresponding to superior hemifield) has substantial damage while the upper half of the retina is relatively healthy. The field test was obtained with a Zeiss-Humphrey Automated Perimeter, a method which can be time-consuming, fatiguing to the patient, and subjective. In FIG. 9, the empirical results clearly correlate with the visual field test. At 625 nm, the transmission value is substantially greater at the 24 mm location of the retina (known to be damaged by the visual field test) than the transmission value at the 0 mm location of the retina (known to healthy by the visual field test). The other values AJHAnton J. HopenAJHAnton J. Hopenin the figure were obtained at intermediate locations.

Figure 10:
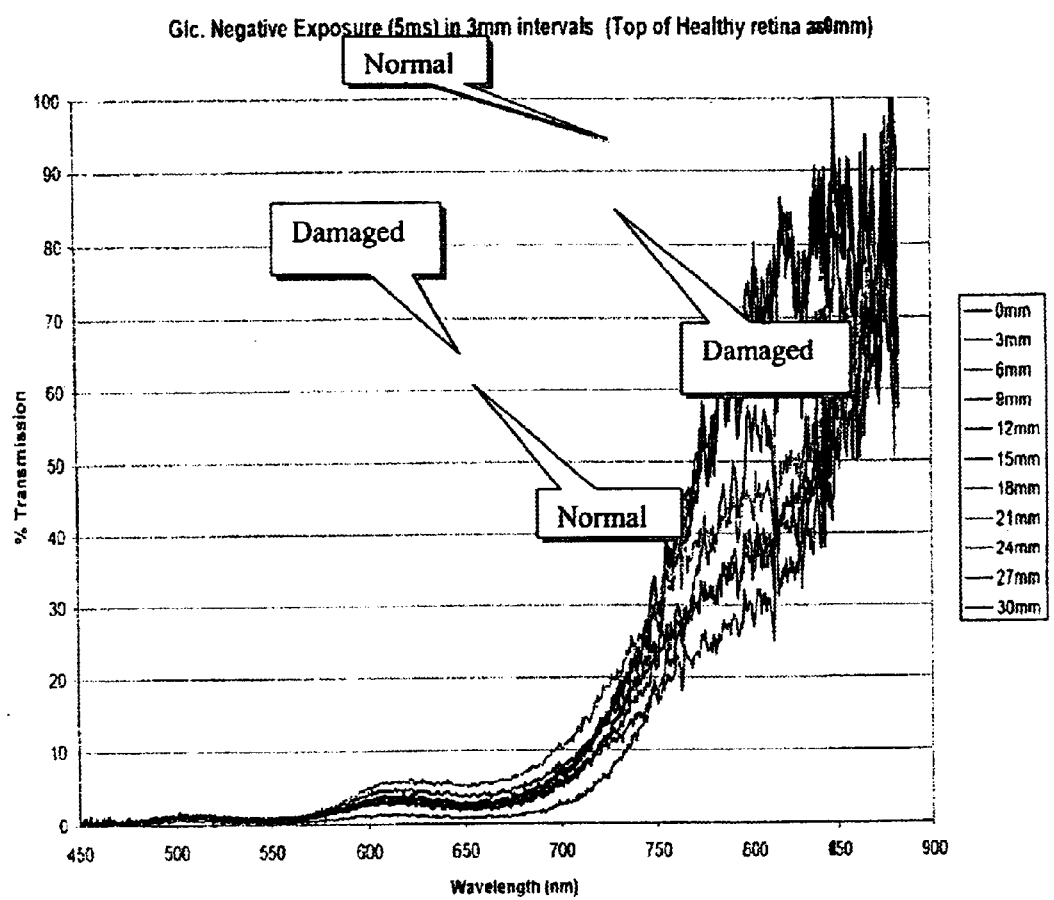
FIG. 10 is the same transmission spectrum of FIG. 9, but zoomed out to provide a full y-axis scale of transmission percentage.
Figure 11:
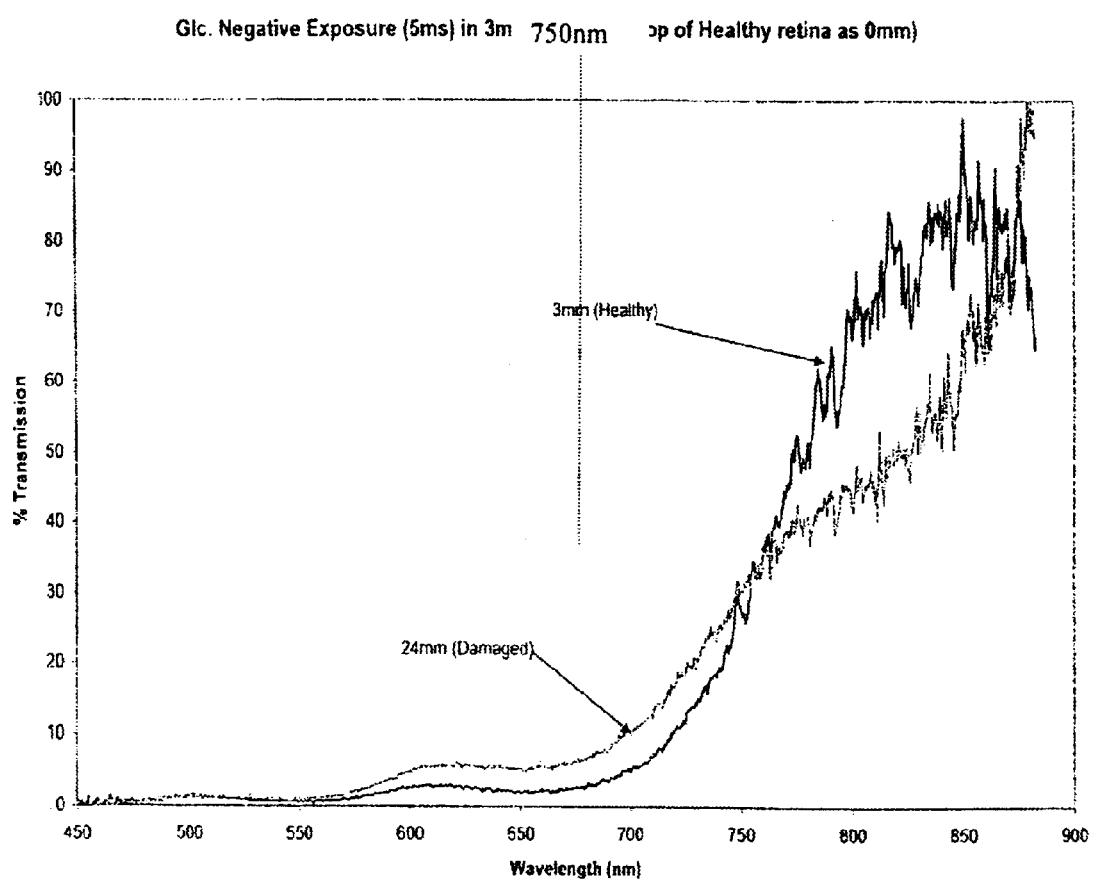
FIG. 11 is the same transmission spectrum of FIGS. 9–10 limited to readings at 24 mm and 3 mm.
Figure 12:
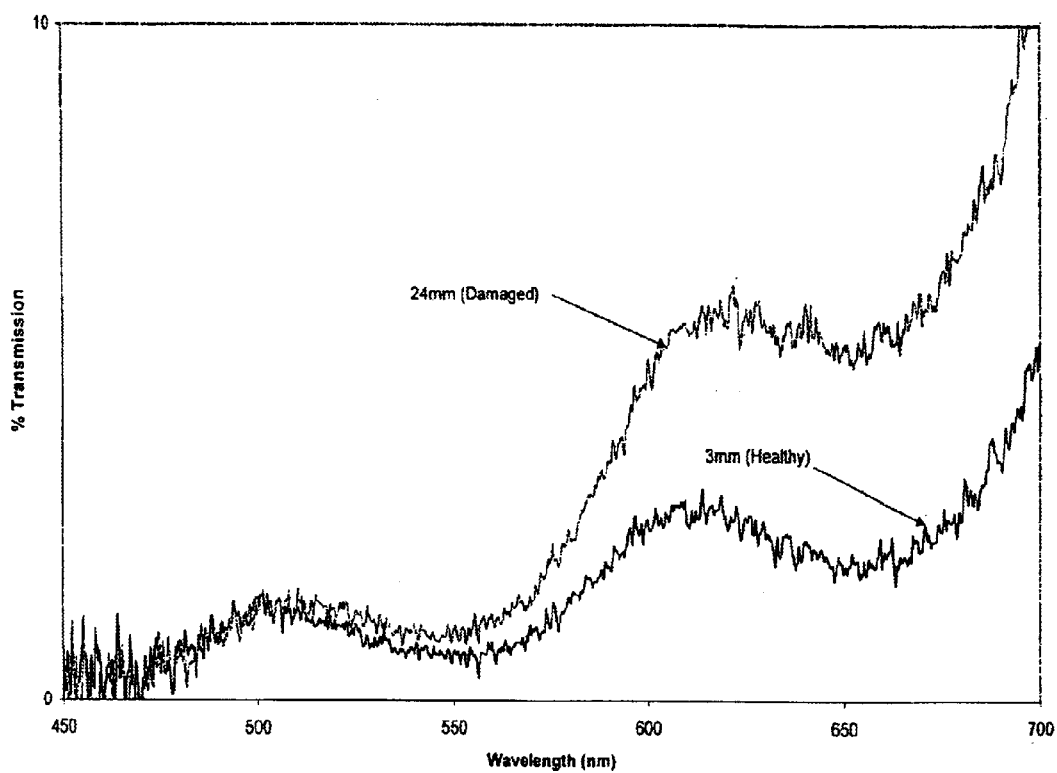
FIG. 12 is the same transmission spectrum of FIG. 11 wherein the graph is zoomed in to show more detail between 450 and 700 nm.

FIG. 10 is the same transmission spectrum of FIG. 9, but zoomed out to provide a full y-axis scale of transmission percentage. It can be seen that below 750 nm, retinal pathology that is damaged produces a greater transmission value than healthy retina, while above 750 nm the inverse is true. FIG. 11 is the same transmission spectrum of FIGS. 9–10 limited to readings at 24 mm and 3 mm which clearly show the inversion of relative transmission strength at 750 nm. FIG. 12 is the same transmission spectrum of FIG. 11 wherein the graph is zoomed in to show more detail between 450 and 700 nm. It can clearly be observed that at 500 nm, the transmission values of healthy and damaged pathology are equal. Thus, values at or near 500 nm may serve as a suitable baseline to calibrate the system for varying reflectivity and/or absorption of individual retinas.

FIG. 13 is a visual field test for the same subject which was used to validate the interpretation of the spectral results. It can be seen that transmission values at numerous wavelengths clearly diverge when damaged pathology is examined. Thus, the present invention advances the art by providing a fully objective, rapid examination of the retina for glaucoma.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of detecting nerve fiber layer and ganglion cell damage representative of glaucoma comprising the steps of:

imaging a human retina in vivo;

measuring a first reflected light intensity at a plurality of locations on the retina at a first predetermined wavelength, wherein measured first values returned from healthy and damaged locations on the retina are substantially identical;

measuring a second reflected light intensity at a plurality of locations on the retina at a second predetermined wavelength, wherein measured second values returned from healthy and damaged locations on the retina substantially diverge; and determining the differences between the first values and the second values at the plurality of locations, wherein a difference between the values is indicative of glaucoma damage.

2. The method of claim 1, further comprising prior to the imaging step, providing a photographic image of the retina.

3. The method of claim 1, wherein the imaging step further comprises:

illuminating the retina with a light source;

passing the image of the retina through a band pass filter; and recording the image of the retina with an image recording means.

4. The method of claim 1, wherein the imaging step further comprises:

illuminating the retina with a light source;

splitting the image of the retina to provide a first image and a second image;

passing the first image through a first filter;

passing the second image through a second filter;

recording the first filtered image with a first image recording means; and recording the second filtered image with a second image recording means.

5. The method of claim 1, wherein the imaging step further comprises:

illuminating the retina with a single-wavelength laser; and recording the image of the retina with an image recording means.

6. The method of claim 1, wherein the imaging step further comprises:

illuminating the retina with a first single-wavelength laser;

illuminating the retina with a second single-wavelength laser;

recording the image resulting from the first laser with a first image recording means; and recording the image resulting from the second laser with a second image recording means.

7. The method of claim 1, wherein the first predetermined wavelength is between 450 nm and 600 nm.

8. The method of claim 1, wherein the second predetermined wavelength is between 750 nm and 875 nm.

9. The method of claim 1, further comprising, prior to the determining step:

normalizing the first values and the second values at the plurality of locations; and spatially overlapping the first values and the second values at the plurality of locations.

10. A system for detecting nerve fiber layer and ganglion cell damage representative of glaucoma, the system comprising:

an image of a human retina in vivo;

a light source adapted to illuminate the image;

means for measuring the reflection intensity at a plurality of locations on the illuminated image at a first wavelength;

means for measuring the reflection intensity at a plurality of locations on the illuminated image at a second wavelength; and computing means for identifying differences between the first and second measured reflection intensities, wherein differences between the reflection intensities is indicative of glaucoma damage.

11. The system of claim 10, wherein the means for measuring the reflection intensity is a spectrometer.

12. A system for detecting nerve fiber layer and ganglion cell damage representative of glaucoma, the system comprising:

a human retina in vivo;

a light source adapted to illuminate the retina;

means for transmitting the illuminated image at a first wavelength of interest;

means for transmitting the illuminated image at a second wavelength of interest;

first image recording means adapted to capture the first resulting image of the retina at a first wavelength of interest;

second image recoding means adapted to capture the second resulting image of the retina at a second wavelength of interest;

computing means for identifying differences between the first resulting image and the second resulting image, wherein differences between the resulting images is indicative of glaucoma damage.

13. The system of claim 12, wherein the means for transmitting the illuminated image at a first wavelength of interest is a band pass filter.

14. The system of claim 12, wherein the means for transmitting the illuminated image at a second wavelength of interest is a band pass filter.

15. The system of claim 12, wherein the means for transmitting the illuminated image at a first wavelength of interest is a laser.

16. The system of claim 12, wherein the means for transmitting the illuminated image at a second wavelength of interest is a laser.

17. The system of claim 12, further comprising, a beam splitter communicatively coupled to the first image recording means and the second image recording means, the beam splitter adapted to provide a first image to the means for transmitting the illuminated image at a first wavelength of interest and a second image to the means for transmitting the illuminated image at a second wavelength of interest.

* * * * *